United States Patent
Morschhäuser et al.

(10) Patent No.: US 6,891,011 B2
(45) Date of Patent: May 10, 2005

(54) COMB-SHAPED COPOLYMERS BASED ON ACRYLOYLDIMETHYLTAURINE ACID

(75) Inventors: Roman Morschhäuser, Mainz (DE); Jan Glauder, Frankfurt (DE); Matthias Löffler, Niedernhausen (DE); Christoph Kayser, Mainz (DE); Aranka Tardi, Neuberg (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/433,179

(22) PCT Filed: Nov. 28, 2001

(86) PCT No.: PCT/EP01/13854

§ 371 (c)(1),
(2), (4) Date: Nov. 10, 2003

(87) PCT Pub. No.: WO02/44224

PCT Pub. Date: Jun. 6, 2002

(65) Prior Publication Data

US 2004/0167304 A1 Aug. 26, 2004

(30) Foreign Application Priority Data

Dec. 1, 2000 (DE) .......................................... 100 59 828

(51) Int. Cl.$^7$ ............................................... C08F 12/30
(52) U.S. Cl. ....................... 526/288; 526/243; 526/245; 526/247; 526/248; 526/287; 526/279; 526/292.2; 526/312
(58) Field of Search ............................... 526/243, 245, 526/247, 248, 287, 288, 279, 292.2, 292.6, 312; 524/458, 461

(56) References Cited

U.S. PATENT DOCUMENTS

| | | | | |
|---|---|---|---|---|
| 4,859,458 A | | 8/1989 | Salamone et al. ............ 424/70 |
| 5,275,809 A | * | 1/1994 | Chen et al. ............... 424/70.16 |
| 5,292,843 A | * | 3/1994 | Jenkins et al. ........... 526/318.5 |
| 5,379,841 A | | 1/1995 | Pusch et al. ................. 166/295 |
| 5,639,841 A | * | 6/1997 | Jenkins ........................ 526/333 |
| 5,725,780 A | * | 3/1998 | Carpenter et al. .......... 210/728 |
| 5,837,789 A | | 11/1998 | Stockhausen et al. ....... 526/320 |
| 6,120,780 A | | 9/2000 | Dupuis et al. ............... 424/401 |
| 6,395,853 B1 | * | 5/2002 | Oswald et al. ........... 526/307.2 |
| 6,403,074 B1 | * | 6/2002 | Blankenburg et al. ... 424/70.12 |
| 6,437,068 B2 | * | 8/2002 | Loffler et al. ............... 526/264 |
| 6,579,417 B1 | * | 6/2003 | Hund et al. ............... 162/164.1 |
| 6,645,476 B1 | * | 11/2003 | Morschhauser et al. ... 424/70.1 |
| 6,702,946 B1 | * | 3/2004 | Huang et al. ............... 210/723 |
| 6,727,318 B1 | * | 4/2004 | Mathauer et al. ........... 524/801 |
| 2004/0109838 A1 | * | 6/2004 | Morschhauser et al. |

FOREIGN PATENT DOCUMENTS

| | | |
|---|---|---|
| DE | 199 07 587 | 8/2000 |
| DE | 199 51 877 | 5/2001 |
| EP | 0 816 403 | 1/1989 |
| EP | 0 356 241 | 2/1990 |
| EP | 0 522 756 | 1/1993 |
| EP | 0558423 A1 * | 9/1993 |
| EP | WO 98/00094 | 1/1998 |
| EP | 1 069 142 | 1/2001 |
| EP | 0 183 184 | 3/2001 |
| WO | WO 99/04750 | 2/1999 |

OTHER PUBLICATIONS

English abstract for DE 19907587, Aug. 24, 2000.
English abstract for EP 1083184, Mar. 14, 2001; and for DE 19951877, May 3, 2001.

* cited by examiner

Primary Examiner—Helen L. Pezzuto
(74) Attorney, Agent, or Firm—Richard P. Silverman

(57) ABSTRACT

The invention provides water-soluble or water-swellable copolymers obtained by free-radical copolymerization of A) acryloyldimethyltaurine and/or acryloyldimethyltaurates, B) optionally, one or more other olefinically unsaturated, nopcationic comonomers, C) optionally, one or more olefinically unsaturated, cationic comonomers, D) optionally, (a) silicon-containing component(s), E) optionally, (a) fluorine-containing component(s), F) optionally, one or more macromonomers, G) the copolymerization taking place in the presence or absence of at least one polymeric additive, H) with the proviso that component A) is copolymerized with at least components selected from at least two of the groups C) to F).

The water-soluble or water-swellable copolymers of the present invention are useful in formulating cosmetics.

22 Claims, No Drawings

COMB-SHAPED COPOLYMERS BASED ON ACRYLOYLDIMETHYLTAURINE ACID

The present invention relates to comb copolymers based on acryloyldimethyltaurine and/or acryloyldimethyltaurates.

In recent years water-soluble polymers have acquired a continually increasing importance in industry and science. In volume terms, polyelectrolytes are occupying a very large proportion of the overall annual production. They find application, for example, in paper processing, in the laundry detergents industry, in textile processing, in petroleum extraction or as important base materials for cosmetics.

In the cosmetics sector a key role is assigned to polyelectrolytes. Besides water-soluble surface-active substances there is a high demand in this sector for systems which thicken oil and water. Thickeners of this kind, particularly the "superabsorbents" prepared on the basis of polyacrylic acid, have progressed since their development in the 1970s to become a pillar of the hygiene sector. In their crosslinked versions, partly or fully neutralized polyacrylic acids and their water-soluble copolymers are employed in numerous cosmetic formulations as bodying agents. The diversity of possible structures and the diverse possible applications associated therewith are manifested not least in a host of patents filed worldwide since the mid-1970s.

In the 1990s, innovative thickeners based on 2-acrylamido-2-methyl-1-propane-sulfonic acid (AMPS) and their salts were introduced into the market (EP 816 403 and WO 98/00094). In both homopolymer and copolymer form (®Aristoflex AVC, Clariant GmbH) such thickeners are superior in many respects to the corresponding polycarboxylates (Carbopols). For example, thickener systems based on AMPS display outstanding properties in pH ranges below pH 6, i.e., in a pH range in which it is no longer possible to operate with conventional polycarboxylate thickeners. Moreover, the microgel structure inherent in the acryloyldimethyltaurine thickeners leads to a particularly pleasant skin sensation.

The ease of processing and the favorable toxicological profile of the principal monomer imbue these thickeners with a high application potential.

Over recent years representatives of a new thickener design have entered the market. In these thickeners, two different properties have been combined in one polymer, thereby opening up new fields of application. Thickening emulsifiers or dispersants are but two examples of this new class of substance. Brand names that may be mentioned include the Pemulens® TR-1 and TR-2 from BF Goodrich or the Aculyn® products from Rohm & Haas. All existing versions are based on hydrophobically modified versions of the conventional polyacrylates.

Surprisingly it has been found that a new class of copolymers based on acryloyldimethyltaurine (AMPS) gives the user the possibility of combining properties of nonpolar moieties, such as alkyl chains or silicone-containing structures, with hydrophilic structural units, such as polyglycols or polyelectrolytes, thereby providing the user in turn with completely new opportunities in formulation technology. The use of the polyfunctional polymers of the invention permits substantial formula simplification for manufacturers of cosmetics, for example.

The invention provides water-soluble or water-swellable copolymers obtainable by free-radical copolymerization of A) acryloyldimethyltaurine and/or acryloyldimethyltaurates, B) if desired, one or more other olefinically unsaturated, noncationic, optionally crosslinking comonomers containing at least one oxygen, nitrogen, sulfur or phosphorus atom and possessing a molecular weight of less than 500 g/mol, C) if desired, one or more olefinically unsaturated, cationic comonomers containing at least one oxygen, nitrogen, sulfur or phosphorus atom and possessing a molecular weight of less than 500 g/mol, D) if desired, one or more at least monofunctional, silicon-containing components capable of free-radical polymerization, E) if desired, one or more at least monofunctional, fluorine-containing components capable of free-radical polymerization, F) if desired, one or more mono- or polyolefinically unsaturated, optionally crosslinking macromonomers each possessing at least one oxygen, nitrogen, sulfur or phosphorus atom and having a number-average molecular weight of greater than or equal to 200 g/mol, the macromonomers not being a silicon-containing component D) or fluorine-containing component E), G) the copolymerization taking place in the presence or absence of at least one polymeric additive having number-average molecular weights of from 200 g/mol to $10^9$ g/mol, H) with the proviso that component A) is copolymerized with at least two components selected from at least two of the groups C) to F).

The copolymers of the invention preferably possess a molecular weight of from $10^3$ g/mol to $10^9$ g/mol, more preferably from $10^4$ to $10^7$ g/mol, very preferably from $5*10^4$ to $5*10^6$ g/mol.

The acryloyldimethyltaurates can be the organic or inorganic salts of acryloyldimethyltaurine. Preference is given to the $Li^+$, $Na^+$, $K^+$, $Mg^{++}$, $Ca^{++}$, $Al^{+++}$ and/or $NH_4^+$ salts. Likewise preferred are the monoalkylammonium, dialkylammonium, trialkylammonium and/or tetraalkylammonium salts, in which the alkyl substituents of the amines may independently of one another be $(C_1-C_{22})$-alkyl radicals or $(C_2-C_{10})$-hydroxyalkyl radicals. Preference is also given to mono- to triethoxylated ammonium compounds with a different degree of ethoxylation. It should be noted that the invention also embraces mixtures of two or more of the abovementioned representatives.

The degree of neutralization of the acryloyldimethyltaurine can be between 0 and 100%, particular preference being given to a degree of neutralization of more than 80%.

Based on the total mass of the copolymers, the amount of acryloyldimethyltaurine and/or acryloyldimethyltaurates is at least 0.1% by weight, preferably from 20 to 99.5% by weight, more preferably from 50 to 98% by weight.

As comonomers B) it is possible to use all olefinically unsaturated noncationic monomers whose reaction parameters allow copolymerization with acryloyldimethyltaurine and/or acryloyldimethyltaurates in the respective reaction media. Preferred comonomers B) are unsaturated carboxylic acids and their anhydrides and salts, and also their esters with aliphatic, olefinic, cycloaliphatic, arylaliphatic or aromatic alcohols having a carbon number of from 1 to 22.

Particularly preferred unsaturated carboxylic acids are acrylic acid, methacrylic acid, styrenesulfonic acid, maleic acid, fumaric acid, crotonic acid, itaconic acid, and senecic acid.

Preferred counterions are $Li^+$, $Na^+$, $K^+$, $Mg^{++}$, $Ca^{++}$, $Al^{+++}$, $NH_4^+$, monoalkylammonium, dialkylammonium, trialkylammonium and/or tetraalkylammonium radicals, in which the alkyl substituents of the amines independently of one another can be ($C_1$–$C_{22}$)-alkyl radicals or ($C_2$–$C_{10}$)-hydroxyalkyl radicals. It is additionally possible to employ mono- to triethoxylated ammonium compounds with a different degree of ethoxylation. The degree of neutralization of the carboxylic acids can be between 0 and 100%. Further preferred comonomers B) are open-chain N-vinyl amides, preferably N-vinylformamide (VIFA), N-vinylmethylformamide, N-vinylmethylacetamide (VIMA) and N-vinylacetamide; cyclic N-vinyl amides (N-vinyl lactams) with a ring size of 3 to 9, preferably N-vinylpyrrolidone (NVP) and N-vinylcaprolactam; amides of acrylic and methacrylic acid, preferably acrylamide, methacrylamide, N,N-dimethylacrylamide, N,N-diethylacrylamide, and N,N-diisopropylacrylamide; alkoxylated acrylamides and methacrylamides, preferably hydroxyethyl methacrylate, hydroxymethylmethacrylamide, hydroxyethylmethacrylamide, hydroxypropylmethacrylamide, and mono [2-(methacryloyloxy)ethyl] succinate; N,N-dimethylamino methacrylate; diethylaminomethyl methacrylate; acrylamido- and methacrylamidoglycolic acid; 2- and 4-vinylpyridine; vinyl acetate; glycidyl methacrylate; styrene; acrylonitrile; vinyl chloride; stearyl acrylate; lauryl methacrylate; vinylidene chloride; and/or tetrafluoroethylene. Likewise suitable comonomers B) are inorganic acids and their salts and esters. Preferred acids are vinylphosphonic acid, vinylsulfonic acid, allylphosphonic acid, and methallylsulfonic acid.

The weight fraction of the comonomers B), based on the total mass of the copolymers, can be from 0 to 99.7% by weight and is preferably from 0.5 to 80% by weight, more preferably from 2 to 50% by weight.

Suitable comonomers C) include all olefinically unsaturated monomers with cationic charge which are capable of forming copolymers with acryloyldimethyltaurine or its salts in the chosen reaction media. The resulting distribution of the cationic charges across the chains can be random, alternating, blocklike or gradientlike. It may be noted that the cationic comonomers C) also comprehend those which bear the cationic charge in the form of a betaine structure. Comonomers C) for the purposes of the invention are also amino-functionalized precursors which can be converted into their corresponding quaternary derivatives by polymer-analogous reactions (e.g., reaction with DMS).
Particularly preferred comonomers C) are
diallyidimethylammonium chloride (DADMAC),
[2-(methacryloyloxy)ethyl]trimethylammonium chloride (MAPTAC),
[2-(acryloyloxy)ethyl]trimethylammonium chloride,
[2-methacrylamidoethyl]trimethylammonium chloride,
[2-(acrylamido)ethyl]trimethylammonium chloride,
N-methyl-2-vinylpyridinium chloride and/or
N-methyl4-vinylpyridinium chloride.

The weight fraction of the comonomers C), based on the total mass of the copolymers, is preferably from 0.1 to 99.8% by weight, more preferably from 0.5 to 30% by weight, and very preferably from 1 to 20% by weight.

Suitable polymerizable silicon-containing components D) are all compounds which are olefinically at least monounsaturated and capable of free-radical copolymerization under the reaction conditions chosen in each case. The distribution of the individual silicone-containing monomers across the polymer chains which form need not necessarily be random. The invention also embraces the formation, for example, of blocklike (including multiblock) or gradientlike structures. Combinations of two or more different silicone-containing representatives are also possible. The use of silicone-containing components having two or more polymerization-active groups leads to the construction of branched or crosslinked structures.

Preferred silicon-containing components are those of formula (I).

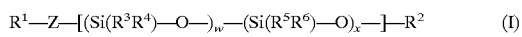

$$R^1\text{—}Z\text{—}[(Si(R^3R^4)\text{—}O\text{—})_w\text{—}(Si(R^5R^6)\text{—}O)_x\text{—}]\text{—}R^2 \quad (I)$$

In this formula $R^1$ represents a polymerizable function from the group of the vinylically unsaturated compounds which is suitable for the synthesis of polymeric structures by a free-radical route. $R^1$ represents preferably a vinyl, allyl, methallyl, methylvinyl, acryloyl ($CH_2$=CH—CO—), methacryloyl ($CH_2$=C[$CH_3$]—CO—), crotonyl, senecionyl, itaconyl, maleyl, fumaryl or styryl radical.

The attachment of the silicone-containing polymer chain to the reactive end group $R^1$ requires a suitable chemical bridge Z. Preferred bridges Z are —O—, —(($C_1$-$C_{50}$)alkylene)—, —(($C_6$-$C_{30}$)arylene)—, —(($C_5$-$C_8$)cycloalkylene)—, —(($C_1$-$C_{50}$)alkenylene)—, —(polypropylene oxide)$_n$—, —(polyethylene oxide)$_o$—, —(polypropylene oxide)$_n$(polyethylene oxide)$_o$—, where n and o independently of one another denote numbers from 0 to 200 and the distribution of the EO/PO units can be random or in the form of blocks. Further suitable bridge groups Z are —(($C_1$-$C_{10}$)alkenyl)-(Si(OCH$_3$)$_2$)— and —(Si(OCH$_3$)$_2$)—.

The polymeric central moiety is represented by silicone-containing repeating units.

The radicals $R^3$, $R^4$, $R^5$, and $R^6$ denote independently of one another —$CH_3$, —O—$CH_3$, —$C_6H_5$ or —O—$C_6H_5$.

The indices w and x represent stoichiometric coefficients which amount independently of one another to from 0 to 500, preferably 10 to 250.

The distribution of the repeating units across the chain can be not only purely random but also blocklike, alternating or gradientlike.

$R^2$ can on the one hand symbolize an aliphatic, olefinic, cycloaliphatic, arylaliphatic or aromatic ($C_1$–$C_{50}$) hydrocarbon radical (linear or branched) or stand for —OH, —$NH_2$, —N($CH_3$)$_2$, —$R^7$ or the structural unit [—Z—$R^1$]. The definition of the two variables Z and $R^1$ has already been explained. $R^7$ stands for further Si-containing groups.

Preferred $R^7$ radicals are —O—Si($CH_3$)$_3$, —O—Si(Ph)$_3$, —O—Si(O—Si($CH_3$)$_3$)$_2$$CH_3$ and —O—Si(O—Si(Ph)$_3$)$_2$Ph.

If $R^2$ is an element of the group [—Z—$R^1$] the monomers in question are difunctional monomers which can be used to crosslink the polymer structures which form. Formula (I) describes not only silicone-containing polymer species with vinylic functionalization and a polymer-typical distribution, but also defined compounds having discrete molecular weights.

Particularly preferred silicone-containing components are the following such components with acrylic or methacrylic modification:

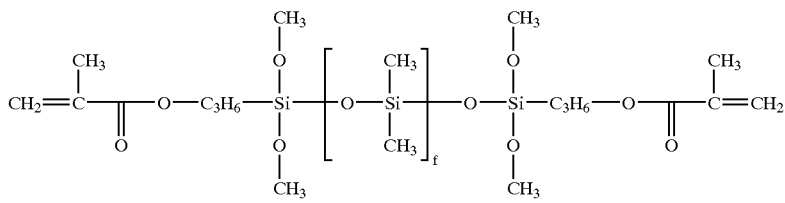

methacryloyloxypropyldimethylsilyl-endblocked polydimethylsiloxanes (f=2 to 500)

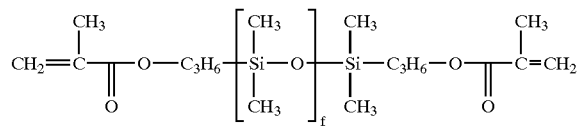

methacryloyloxypropyl-endblocked polydimethylsiloxanes (f=2 to 500)

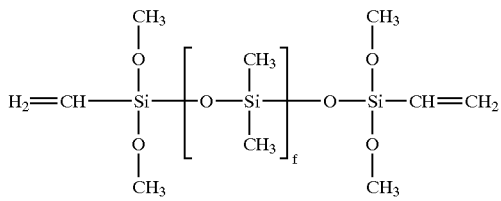

vinyldimethoxysilyl-endblocked polydimethylsiloxanes (f=2-500)

Based on the total mass of the copolymers, the weight fraction of the comonomers D) can be from 0.1 to 99.8% by weight, preferably from 0.1 to 50% by weight, more preferably from 0.2 to 40% by weight, very preferably from 0.5 to 30% by weight.

Suitable polymerizable fluorine-containing components E) include all compounds which are olefinically at least monounsaturated and which are capable of free-radical copolymerization under the reaction conditions chosen in each case. The distribution of the individual fluorine-containing monomers across the polymer chains which form need not necessarily be random. The invention also embraces the formation of blocklike (including multiblock) or gradientlike structures, for example. Combinations of two or more different fluorine-containing components E) are also possible, it being clear to the expert that monofunctional representatives lead to the formation of comb-shaped structures while di-, tri-, or polyfunctional components E) lead to structures which are at least partly crosslinked.

Preferred fluorine-containing components E) are those of formula (II).

$$R^1-Y-C_rH_{2r}C_5F_{2s}CF_3 \qquad (II)$$

In this formula $R^1$ represents a polymerizable function from the group of the vinylically unsaturated compounds which is suitable for the construction of polymeric structures by a free-radical route. $R^1$ is preferably a vinyl, allyl, methallyl, methylvinyl, acryloyl ($CH_2$=CH—CO—), methacryloyl ($CH_2$=C[$CH_3$]—CO—), crotonyl, senecionyl, itaconyl, maleyl, fumaryl or styryl radical, more preferably an acryloyl or methacryloyl radical.

The attachment of the fluorine-containing group to the reactive end group $R^1$ requires a suitable chemical bridge Y.

Preferred bridges Y are —O—, —C(O)—, —C(O)—O—, —S—, —O—$CH_2$—CH(O—)—$CH_2$OH, —O—$CH_2$—CH(OH)—$CH_2$—O—, —O—$SO_2$—O—, —O—S(O)—O—, —PH—, —P($CH_3$)—, —$PO_3$—, —NH—, —N($CH_3$)—, —O—($C_1$-$C_{50}$)alkyl-O—, —O-phenyl-O—, —O-benzyl-O—, —O—($C_5$-$C_8$)cycloalkyl-O—, —O—($C_1$-$C_{50}$)alkenyl-O—, —O—(CH($CH_3$)—$CH_2$—O)$_n$—, —O—($CH_2$—$CH_2$—O)$_n$—, and —O—([CH—$CH_2$—O]$_n$—[$CH_2$—$CH_2$—O]$_m$)$_o$—, where n, m, and o independently of one another denote numbers from 0 to 200 and the distribution of the EO and PO units can be random or in the form of blocks.

r and s are stoichiometric coefficients which independently of one another denote numbers from 0 to 200.

Particularly preferred fluorine-containing components are
perfluorohexylethanol methacrylate,
perfluorohexoylpropanol methacrylate,
perfluoroctylethanol methacrylate,
perfluoroctylpropanol methacrylate,
perfluorohexylethanolyl polyglycol ether methacrylate,
perfluorohexoylpropanolyl poly[ethylglycol-co-propylene glycol ether] acrylate,
perfluoroctylethanolyl poly[ethylglycol-block-co-propylene glycol ether]
methacrylate,
and/or
perfluoroctylpropanolyl polypropylene glycol ether methacrylate.

Based on the total mass of the copolymers, the weight fraction of the comonomers E) can be from 0.1 to 99.8% by weight, preferably from 0.1 to 50% by weight, more preferably from 0.2 to 30% by weight, very preferably from 0.5 to 20% by weight.

The macromonomers F) are at least singly olefinically functionalized polymers having one or more discrete repeating units and a number-average molecular weight of greater than or equal to 200 g/mol. In the copolymerization it is also possible to use mixtures of chemically different macromonomers F). The macromonomers are polymeric structures composed of one or more repeating units and have a molecular weight distribution characteristic of polymers.

Preferred macromonomers F) are compounds of formula (III).

$$R^1-Y-[(A)_v-(B)_w-(C)_x-(D)_z]-R^2 \qquad (III)$$

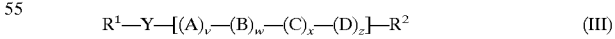

$R^1$ represents a polymerizable function from the group of the vinylically unsaturated compounds which are suitable for constructing polymeric structures by a free-radical route. Preferably $R^1$ is a vinyl, allyl, methallyl, methylvinyl, acryloyl ($CH_2$=CH—CO—), methacryloyl ($CH_2$=C[$CH_3$]—CO—), crotonyl, senecionyl, itaconyl, maleyl, fumaryl or styryl radical.

Attachment of the polymer chain to the reactive end group requires a suitable bridging group Y. Preferred bridges Y are —O—, —C(O)—, —C(O)—O—, —S—, —O—$CH_2$—CH(O—)—$CH_2$OH, —O—$CH_2$—CH(OH)—$CH_2$O—, —O—SO$_2$—O—, —O—SO$_2$—O—, —O—SO—O—, —PH—, —P(CH$_3$)—, —PO$_3$—, —NH—, and —N(CH$_3$)—, more preferably —O—.

The polymeric central moiety of the macromonomer is represented by the discrete repeating units A, B, C, and D. Preferred repeating units A, B, C, and D are derived from acrylamide, methacrylamide, ethylene oxide, propylene oxide, AMPS, acrylic acid, methacrylic acid, methyl methacrylate, acrylonitrile, maleic acid, vinyl acetate, styrene, 1,3-butadiene, isoprene, isobutene, diethylacrylamide, and diisopropylacrylamide.

The indices v, w, x, and z in formula (III) represent the stoichiometric coefficients relating to the repeating units A, B, C, and D, v, w, x, and z amount independently of one another to from 0 to 500, preferably 1 to 30, it being necessary for the sum of the four coefficients on average to be ≧1.

The distribution of the repeating units over the macromonomer chain can be random, blocklike, alternating or gradientlike.

$R^2$ denotes a linear or branched aliphatic, olefinic, cycloaliphatic, arylaliphatic or aromatic ($C_1$–$C_{50}$) hydrocarbon radical, OH, —NH$_2$, —N(CH$_3$)$_2$ or is the structural unit [—Y—$R^1$].

In the case of $R^2$ being [—Y—$R^1$] the macromonomers in question are difunctional and suitable for crosslinking the copolymers.

Particularly preferred macromonomers F) are acrylically or methacrylically monofunctionalized alkyl ethoxylates of formula (IV).

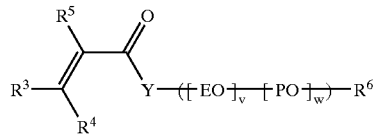

(IV)

$R^3$, $R^4$, $R^5$, and $R^6$ are independently of one another hydrogen or n-aliphatic, iso-aliphatic, olefinic, cycloaliphatic, arylaliphatic or aromatic ($C_1$–$C_{30}$) hydrocarbon radicals.

Preferably $R^3$ and $R^4$ are H or —CH$_3$, more preferably H; $R^5$ is H or —CH$_3$; and $R^6$ is an n-aliphatic, iso-aliphatic, olefinic, cycloaliphatic, arylaliphatic or aromatic ($C_1$–$C_{30}$) hydrocarbon radical. v and w are in turn the stoichiometric coefficients relating to the ethylene oxide units (EO) and propylene oxide units (PO). v and w amount independently of one another to from 0 to 500, preferably 1 to 30, it being necessary for the sum of v and w to be on average ≧1. The distribution of the EO and PO units over the macromonomer chain can be random, blocklike, alternating or gradientlike. Y stands for the abovementioned bridges, preferably —O—.

Particularly preferred macromonomers F) have the following structure in accordance with formula (IV):

| Name | $R^3$ | $R^4$ | $R^5$ | $R^6$ | v | w |
|---|---|---|---|---|---|---|
| ® LA-030 methacrylate | H | H | —CH$_3$ | -lauryl | 3 | 0 |
| ® LA-070 methacrylate | H | H | —CH$_3$ | -lauryl | 7 | 0 |
| ® LA-200 methacrylate | H | H | —CH$_3$ | -lauryl | 20 | 0 |
| ® LA-250 methacrylate | H | H | —CH$_3$ | -lauryl | 25 | 0 |
| ® T-080 methacrylate | H | H | —CH$_3$ | -talc | 8 | 0 |
| ® T-080 acrylate | H | H | H | -talc | 8 | 0 |
| ® T-250 methacrylate | H | H | —CH$_3$ | -talc | 25 | 0 |
| ® T-250 crotonate | —CH$_3$ | H | —CH$_3$ | -talc | 25 | 0 |
| ® OC-030 methacrylate | H | H | —CH$_3$ | -octyl | 3 | 0 |
| ® OC-105 methacrylate | H | H | —CH$_3$ | -octyl | 10 | 5 |
| ® Behenyl-010-methylaryl | H | H | H | -behenyl | 10 | 0 |
| ® Behenyl-020-methylaryl | H | H | H | -behenyl | 20 | 0 |
| ® Behenyl-010-senecionyl | —CH$_3$ | —CH$_3$ | H | -behenyl | 10 | 0 |
| ® PEG-440 diacrylate | H | H | H | -acryloyl | 10 | 0 |
| ® B-11-50 methacrylate | H | H | —CH$_3$ | -butyl | 17 | 13 |
| ® MPEG-750 methacrylate | H | H | —CH$_3$ | -methyl | 18 | 0 |
| ® P-010 acrylate | H | H | H | -phenyl | 10 | 0 |
| ® O-050 acrylate | H | H | H | -oleyl | 5 | 0 |

The molecular weight of the macromonomers F) is preferably from 200 g/mol to $10^6$ g/mol, more preferably from 150 to $10^4$ g/mol, and very preferably from 200 to 5000 g/mol.

Based on the total mass of the copolymers, the weight fraction of the macromonomer F) can be from 0.1 to 99.8% by weight, more preferably from 2 to 90% by weight, very preferably from 5 to 80% by weight.

Preferred copolymers are those obtainable by copolymerizing at least components A), C), and D).

Further preferred copolymers are those obtainable by copolymerizing at least components A), C), and E).

Further preferred copolymers are those obtainable by copolymerizing at least components A), C), and F).

Further preferred copolymers are those obtainable by copolymerizing at least components A), D), and F).

Further preferred copolymers are those obtainable by copolymerizing at least components A), E), and F).

Further preferred copolymers are those obtainable by copolymerizing at least components A), B), D), and F).

Further preferred copolymers are those obtainable by copolymerizing at least components A), B), C), D), and F).

In one preferred embodiment the copolymerization is conducted in the presence of at least one polymeric additive G), the additive G) being added wholly or partly in solution to the polymerization medium before the actual copolymerization. The use of two or more additives G) is likewise in accordance with the invention.

Crosslinked additives G) may likewise be used.

The additives G) or mixtures thereof must only be wholly or partly soluble in the chosen polymerization medium. During the actual polymerization step the additive G) has a number of functions. On the one hand it prevents the formation of overcrosslinked polymer fractions in the copolymer which forms in the actual polymerization step, and on the other hand the additive G) is statistically attacked by active free radicals in accordance with the very well-known mechanism of graft copolymerization. Depending on the particular additive G), this results in greater or lesser fractions of the additive being incorporated into the copolymers. Moreover, suitable additives G) possess the property of altering the solution parameters of the copolymers which form during the free-radical polymerization reaction in such a way that the average molecular weights are shifted to higher values. As compared with analogous copolymers prepared without the addition of the additives G), those prepared with the addition of additives G) advantageously exhibit a significantly higher viscosity in aqueous solution.

Preferred additives G) are homopolymers and copolymers which are soluble in water and/or alcohols. The term "copolymers" also comprehends those having more than two different monomer types.

Particularly preferred additives G) are homopolymers and copolymers of N-vinyl-formamide, N-vinylacetamide, N-vinylpyrrolidone, ethylene oxide, propylene oxide, acryloyldimethyltaurine, N-vinylcaprolactam, N-vinylmethylacetamide, acrylamide, acrylic acid, methacrylic acid, N-vinylmorpholide, hydroxyethyl methacrylate, diallyldimethylammonium chloride (DADMAC) and/or [2-(methacryloyloxy)ethyl] trimethylammonium chloride (MAPTAC); polyalkylene glycols and/or alkylpolyglycols.

Particularly preferred additives G) are polyvinylpyrrolidones (e.g., K15®, K20® and K30® from BASF), poly(N-vinylformamides), poly(N-vinylcaprolactams), and copolymers of N-vinylpyrrolidone, N-vinylformamide and/or acrylic acid, which may also have been partly or fully hydrolyzed.

The molecular weight of the additives G) is preferably from $10^2$ to $10^7$ g/mol, more preferably from $0.5*10^4$ to $10^6$ g/mol.

The amount in which the polymeric additive G) is used, based on the total mass of the monomers to be polymerized during the copolymerization, is preferably from 0.1 to 90% by weight, more preferably from 1 to 20% by weight, and with particular preference from 1.5 to 10% by weight.

In a further preferred embodiment the copolymers of the invention are crosslinked, i.e., they contain comonomers having at least two polymerizable vinyl groups. Preferred crosslinkers are methylenebisacrylamide; methylenebismethacrylamide; esters of unsaturated monocarboxylic and polycarboxylic acids with polyols, preferably di-acrylates and tri-acrylates and -methacrylates, preferably butanediol and ethylene glycol diacrylate and -methacrylate, trimethylolpropane triacrylate (TMPTA) and trimethylolpropane trimethacrylate (TMPTMA); allyl compounds, preferably allyl (meth)acrylate, triallyl cyanurate, diallyl maleate, polyallyl esters, tetraallyloxyethane, triallylamine, tetraallylethylenediamine; allyl esters of phosphoric acid; and/or vinylphosphonic acid derivatives.

A particularly preferred crosslinker is trimethylolpropane triacrylate (TMPTA). The weight fraction of crosslinking comonomers, based on the total amount of the copolymers, is preferably up to 20% by weight, more preferably from 0.05 to 10% by weight, and with particular preference from 0.1 to 7% by weight.

The polymerization medium used may comprise all organic or inorganic solvents which have a very substantially inert behavior with respect to free-radical polymerization reactions and which advantageously allow the formation of medium or high molecular weights. Those used preferably include water; lower alcohols; preferably methanol, ethanol, propanols, iso-, sec- and t-butanol, very preferably t-butanol; hydrocarbons having 1 to 30 carbon atoms, and mixtures of the aforementioned compounds.

The polymerization reaction takes place preferably in the temperature range between 0 and 150° C., more preferably between 10 and 100° C., either at atmospheric pressure or under elevated or reduced pressure. If desired the polymerization may also be performed under an inert gas atmosphere, preferably under nitrogen.

In order to initiate the polymerization it is possible to use high-energy electro-magnetic rays, mechanical energy, or the customary chemical polymerization initiators, such as organic peroxides, e.g., benzoyl peroxide, tert-butyl hydroperoxide, methyl ethyl ketone peroxide, cumene hydroperoxide, dilauroyl peroxide or azo initiators, such as azodiisobutyronitrile (AIBN), for example.

Likewise suitable are inorganic peroxy compounds, such as $(NH_4)_2S_2O_8$, $K_2S_2O_8$ or $H_2O_2$, for example, where appropriate in combination with reducing agents (e.g., sodium hydrogensulfite, ascorbic acid, iron(II) sulfate, etc.) or redox systems comprising as reducing component an aliphatic or aromatic sulfonic acid (e.g., benzenesulfonic acid, toluenesulfonic acid, etc.).

The polymerization reaction can be conducted, for example, as a precipitation polymerization, emulsion polymerization, bulk polymerization, solution polymerization or gel polymerization. Particularly advantageous for the profile of properties of the copolymers of the invention is precipitation polymerization, preferably in tert-butanol.

The polyfunctional polymers of the invention possess a great structural diversity and, consequently, broad potential possibilities for use, which can be tailored to virtually any task where interface effects and/or surface effects play a part. Attention is drawn in particular to the high potential for application in the field of cosmetology, e.g., as thickeners and emulsifiers. The term "custom-tailored polymers" vividly describes the possibilities which this new class of polymer provides to the user.

The following examples serve to illustrate the invention without, however, restricting it thereto.

EXAMPLE 1

| Reactants | amount (g) |
| --- | --- |
| $NH_3$-neutralized AMPS | 80 |
| Genapol-LA-070-methacrylate | 10 |
| Monofunctionalized ethoxylated siloxane (methacrylic, ® Silvet 7608 WITCO) | 10 |
| TMPTA | 1.8 |
| t-Butanol | 500 |
| Dilauroyl peroxide (initiator) | 1 |

The polymer was prepared by the precipitation method in tert-butanol. The monomers in t-butanol were introduced as an initial charge and the reaction mixture was rendered inert, and then, after initial heating, the reaction was initiated by addition of DLP. The polymer was isolated by removing the solvent under suction and by subsequent vacuum drying.

EXAMPLE 2

| Reactants | amount (g) |
| --- | --- |
| $NH_3$-neutralized AMPS | 70 |
| N-Vinylpyrrolidone | 5 |
| ® Genapol-T-250 methacrylate | 15 |
| [2-(Methacryloyloxy)ethyl]trimethylammonium chloride | 10 |
| Water | 500 |
| $Na_2S_2O_8$ (initiator) | 1 |
| Poly-N-vinylpyrrolidone (® K-30, BASF) | 10 |

The polymer was prepared by the gel polymerization method in water. The monomers were dissolved in water, the reaction mixture was rendered inert, and then, after initial heating, the reaction was initiated by addition of sodium peroxodisulfate. The polymer gel was subsequently comminuted and the polymer was isolated by vacuum drying.

EXAMPLE 3

| Reactants | amount (g) |
|---|---|
| AMPS | 60 |
| ® Genapol-BE-020 methacrylate | 10 |
| ® Genapol-T-250 acrylate | 10 |
| [2-Methacrylamido)ethyl]trimethylammonium chloride | 20 |
| Cyclohexane | 200 |
| Water | 300 |
| Span 80 | 1 |
| $Na_2S_2O_8$ (initiator) | 1 |

The polymer was prepared by the emulsion method in water. The monomers were emulsified in water/cyclohexane using ®Span 80, the reaction mixture was rendered inert using $N_2$, and then, after initial heating, the reaction was initiated by addition of sodium peroxodisulfate. The polymer emulsion was subsequently evaporated down (cyclohexane acting as azeotrope former for water) and by this means the polymer was isolated.

EXAMPLE 4

| Reactants | amount (g) |
|---|---|
| $NH_3$-neutralized AMPS | 60 |
| ® PEG-750 methacrylate | 20 |
| Methacryloyloxypropyldimethicone (® GP-478, Genesee Pol. Corp.) | 10 |
| Perfluoroctyl polyethylene glycol methacrylate | 10 |
| t-Butanol | 500 |
| AIBN (initiator) | 1 |
| Poly[N-vinylcaprolactone-co-acrylic acid] (10/90) | 10 |

The polymer was prepared by the precipitation method in tert-butanol. The monomers in t-butanol were introduced as an initial charge and the reaction mixture was rendered inert, and then, after initial heating, the reaction was initiated by addition of AIBN. The polymer was isolated by removing the solvent under suction and by subsequent vacuum drying.

EXAMPLE 5

| Reactants | amount (g) |
|---|---|
| Na-neutralized AMPS | 80 |
| N-Vinylformamide | 5 |
| ®Genapol-O-150 methacrylate | 5 |
| Diallyldimethylammonium chloride (DADMAC) | 10 |
| Water | 300 |
| TMPTA | 1.8 |
| $H_2O_2$/iron (initiator) | 1 |
| Poly[N-vinylformamide] | 8 |

The polymer was prepared by the solution method in water. The monomers were dissolved in water, the reaction mixture was rendered inert, and then, after initial heating, the reaction was initiated by means of a suitable redox couple. The polymer solution was subsequently evaporated down and the polymer was then isolated by vacuum drying.

EXAMPLE 6

| Reactants | amount (g) |
|---|---|
| $NH_3$-neutralized AMPS | 70 |
| ® Genapol-T-250 acrylate | 10 |
| N-Methyl-4-vinylpyridinium chloride | 5 |
| Monofunctionalized (methacrylically) ethyoxylated siloxane (® Silvet Y-12867, WITCO) | 2.5 |
| Perfluorohexyl polyethylene glycol methacrylate | 2.5 |
| Polyethylene glycol dimethacrylate ($M_n$ = 5 000 g/mol) | 10 |
| t-Butanol | 500 |
| Dilauroyl peroxide | 2 |
| Poly[N-vinylcaprolactam] | 4 |

The polymer was prepared by the precipitation method in tert-butanol. The monomers in t-butanol were introduced as an initial charge and the reaction mixture was rendered inert, and then, after initial heating, the reaction was initiated by addition of DLP. The polymer was isolated by removal of the solvent under suction and by subsequent vacuum drying.

EXAMPLE 7

| Reactants | amount (g) |
|---|---|
| $NH_3$-neutralized AMPS | 10 |
| Acrylamide | 20 |
| N-2-Vinylpyrrolidone | 30 |
| Monofunctionalized (methacrylically) ethyoxylated Siloxane (® Silvet 7608 WITCO) | 20 |
| Methacryloyloxypropyldimethicone (® GP-446, Genesee Pol. Corp.) | 10 |
| ®Fluowet AC 812 | 10 |
| t-Butanol | 500 |
| Dilauroyl peroxide | 2 |

The polymer was prepared by the solution method in tert-butanol. The monomers in t-butanol were introduced as an initial charge, the reaction mixture was rendered inert, and then, after initial heating, the reaction was initiated by addition of DLP. The polymer was isolated by evaporation of the solvent and by subsequent vacuum drying.

EXAMPLE 8

| Reactants | amount (g) |
|---|---|
| $NH_3$-neutralized AMPS | 60 |
| Diallyldimethylammonium chloride (DADMAC) | 10 |
| [2-(Methacryloyloxy)ethyl]trimethylammonium chloride | 10 |
| ®Genapol-LA-250 crotonate | 10 |
| Methacryloyloxypropyldimethicone (® GP-478, Genesee Pol. Corp.) | 10 |
| Isopropanol | 300 |
| Water | 200 |
| Potassium peroxodisulfate | 2 |
| Poly[acrylic acid-co-N-vinylformamide] | 7 |

The polymer was prepared by the solution method in an isopropanol/water mixture. The monomers were introduced in isopropanol/water, the reaction mixture was rendered inert, and then, after initial heating, the reaction was initiated by addition of potassium peroxodisulfate. The polymer was isolated by evaporation of the solvent mixture and by subsequent vacuum drying.

What is claimed is:

1. A water-soluble or water-swellable copolymer obtained by free-radical copolymerization of
   A) 50 to 99% by weight of acryloyldimethyltaurine and/or acryloyldimethyltaurine based on a total weight of said copolymer, said acryloyldimethyltaurine and/or acryloyldimethyltaurine having a degree of neutralization of more than 80%,
   B) optionally, one or more other olefinically unsaturated, noncationic, comonomer containing at least one oxygen, nitrogen, sulfur or phosphorus atom and having a molecular weight of less than 500 g/mol,
   C) one or more olefinically unsaturated, cationic comonomer containing at least one oxygen, nitrogen, sulfur or phosphorus atom and having a molecular weight of less than 500 g/mol,
   D) optionally, one or more at least monofunctional, silicon-containing components capable of free-radical polymerization,
   E) optionally, one or more at least monofunctional, fluorine-containing components capable of free-radical polymerization,
   F) optionally, one or more mono- or polyolefinically unsaturated, optionally crosslinking macromonomers each possessing at least one oxygen, nitrogen, sulfur or phosphorus atom and having a number-average molecular weight of greater than or equal to 200 g/mol, the macromonomers not being a silicon-containing component D) or fluorine-containing component E),
   G) the copolymerization taking place in the absence of at least one polymeric additive having number-average molecular weight of from 200 g/mol to $10^9$ g/mol.
   H) with the proviso that component A) is copolymerized with at least two components selected from at least two of the groups C) to F).

2. The water-soluble or water-swellable copolymer as claimed in claim 1, wherein the comonomer B) is selected from the group consisting of unsaturated carboxylic acids, salts of unsaturated carboxylic acids, anhydrides of unsaturated carboxylic acids, esters of unsaturated carboxylic acids with aliphatic, olefinic, cycloaliphatic, arylaliphatic or aromatic alcohols having 1 to 22 carbon atoms, open-chain N-vinyl amides, cyclic N-vinyl amides having a ring size of from 3 to 9, amides of acrylic acid, amides of methacrylic acid, amides of substituted acrylic acids, amides of substituted methacrylic acids, 2-vinylpyridine, 4-vinylpyridine, vinyl acetate; styrene, acrylonitrile, vinyl chloride, vinylidene chloride, tetrafluoroethylene, vinylphosphonic acid or the esters or salts thereof, vinylsulfonic acid or the esters or salts thereof, allylphosphonic acid or the esters or salts thereof, methallylsulfonic acid or the esters or salts thereof, and mixtures thereof.

3. The water-soluble or water-swellable copolymer as claimed in claim 1, wherein the comonomer C) is selected from the group consisting of diallyldimethylammonium chloride,
   [2-(methacryloyloxy)ethyl]trimethylammonium chloride,
   [2-(acryloyloxy)ethyl]trimethylammonium chloride,
   [2-methacrylamidoethyl]trimethylammonium chloride,
   [2-(acrylamido)ethyl]trimethylammonium chloride,
   N-methyl-2-vinylpyridinium chloride,
   N-methyl-4-vinylpyridinium chloride, and mixtures thereof.

4. The water-soluble or water-swellable copolymer of claim 1, wherein the silicon-containing component D) is a compound of formula (I)

$$R^1-Z-[(Si(R^3R^4)-O-)_w-(Si(R^8R^8)-O)_x-]-R^2 \quad (I)$$

where
   $R^1$ is a radical selected from the group consisting of vinyl, allyl, methallyl, methylvinyl, acryloyl, methacryloyl, crotonyl, senecionyl, itaconyl, maleyl, fumaryl, styryl, and mixtures thereof;
   Z is a chemical bridge,
   $R^3$, $R^4$, $R^5$, and $R^6$ independently of one another are $-CH_3$, $-O-CH_3$, $-C_6H_5$ or $-O-C_6H_5$;
   w, x denote numbers from 0 to 500, it being necessary for either w or x to be greater than zero; and
   $R^2$ is a saturated or unsaturated aliphatic, cycloaliphatic, arylaliphatic or aromatic radical having in each case 1 to 50 carbon atoms or a group of the formulae $-OH$, $-NH_2$, $-N(CH_3)_2$, $-R^7$ or a group $-Z-R^1$, where Z and $R^1$ are as defined above and
   $R^7$ is selected from the group consisting of $-O-Si(CH_3)_3$, $-O-Si(phenyl)_3$, $-O-(Si(O-Si(CH_3)_3)_2CH_3$, and $-O-Si(O--Si(phenyl)_3)_2phenyl$.

5. The water-soluble or water-swellable copolymer of claim 1, wherein the fluorine-containing component E) is a compound of formula (II)

$$R^1-Y-C_rH_{2r}C_sF_{2s}CF_3 \quad (II)$$

where
   $R^1$ represents a polymerizable function from a vinylically unsaturated compound:
   Y is a chemical bridge, and
   r, s are stoichiometric coefficients which independently of one another can be numbers between 0 and 200.

6. The water-soluble or water-swellable copolymer of claim 1, wherein the-macromonomer F) is a compound of formula (III)

$$R^1-Y-[(A)_v-(B)_w-(C)_x-(D)_z]-R^2 \quad (III)$$

where $R^1$ is a polymerizable function from a vinylically unsaturated compound;
   Y is a bridging group,
   A, B, C, and D independently of one another are discrete chemical repeating units,
   v, w, x, and z independently of one another amount to from 0 to 500, the sum of v, w, x, and z being on average $\geq 1$; and
   $R^2$ is a linear or branched aliphatic, olefinic, cycloaliphatic, arylaliphatic or aromatic ($C_1$-$C_{50}$) hydrocarbon radical, OH, $-NH_2$ or $-N(CH_3)_2$ or is $[-Y-R^1]$.

7. The water-soluble or water-swellable copolymer of claim 1, wherein the polymeric additive G) is selected from the group consisting of polyalkylene glycol, alkylpolyglycol, and mixtures thereof or a homopolymer or copolymer of a compound selected from the group consisting of N-vinylformamide, N-vinylacetamide, N-vinylpyrrolldone, ethylene oxide, propylene oxide, acryloyldimethyltaurine, N-vinylcaprolactam, N-vinylmethylacetamide, acrylamide, acrylic acid, methacrylic acid, N-vinylmorpholide, hydroxymethyl methacrylate, diallyldimethylammonium chloride (DADMAC), [2-(methacryloyloxy)ethyl]trimethylammonium chloride (MAPTAC), and mixtures thereof.

8. The water-soluble or water-swellable copolymer of claim 1, wherein the copolymer is crosslinked.

9. The water-soluble or water-swellable copolymer of claim 1, wherein the copolymerization is prepared by precipitation polymerization in tert-butanol.

10. The water-soluble or water-swellable copolymer of claim 4, wherein the chemical bridge, Z, is selected from the group consisting of —O—; —(($C_1$-$C_{60}$)alkylene)—; —(($C_1$-$C_{30}$)arylene)—; —(($C_5$-$C_8$) cycloalkylene—; —(($C_1$-$C_{50}$)alkenylene—; —(polypropylene oxide)$_o$—; —(polyethylene oxide)$_o$—; —(polypropylene oxide)$_n$—(polyethylene oxide)$_o$—; where n and o independently of one another denote numbers from 0 to 200 and the distribution of the EO/PO units can be random or in block form.

11. The water-soluble or water-swellable copolymer of claim 4, wherein the chemical bridge, Z, is —(($C_1$-$C_{10}$)alkyl-Si(OCH$_3$)$_2$)— and/or —(Si(OCH$_3$)$_2$)—.

12. The water-soluble or water-swellable copolymer of claim 5, wherein $R^1$ is a radical selected from the group consisting of vinyl, allyl, methallyl, methylvinyl, acryloyl, methacryloyl, crotonyl, senecionyl, itaconyl, maleyl, fumaryl, styryl, and mixtures thereof.

13. The water-soluble or water-swellable copolymer of claim 5, wherein the chemical bridge, Y, is selected from the group consisting of —O—; —C(O)—; —C(O)—O—; —S—; —O—CH$_2$—CH(O—)—CH$_2$OH; —O—CH$_2$—CH(OH)—CH$_2$—O—; —O—SO$_2$—O—; —O—S(O)—O—; —PH—; —P(CH$_3$)—; —PO$_3$—; —NH—; —N(CH$_3$)—; —O—($C_1$-$C_{50}$)alkyl-O—; —O-phenyl-O—; —O-benzyl-O—; —O—($C_5$-$C_8$)cycloalkyl-O—; —O—($C_1$-$C_{50}$)alkenyl-O—; —O—(CH(CH$_3$)—CH$_2$—O)$_n$—, —O—(CH$_2$—CH$_2$—O)$_n$—; and —O—([CH—CH$_2$—O]$_n$—[CH$_2$—CH$_2$—O]$_m$)$_o$—, where n, m, and o independently of one another denote numbers from 0 to 200.

14. The water-soluble or water-swellable copolymer of claim 6, wherein $R^1$ is a radical selected from the group consisting of vinyl, allyl, methallyl, methylvinyl, acryloyl, methacryloyl, crotonyl, senecionyl, itaconyl, maleyl, fumaryl, styryl, and mixtures thereof.

15. The water-soluble or water-swellable copolymer of claim 6, wherein the chemical bridge Y is selected from the group consisting of O—, —S—, —C(O)—, —C(O)—O—, —O—CH$_2$—CH(O—)—CH$_2$OH, —O—CH$_2$—CH(OH)—CH$_2$O—, —O—SO$_2$—O—, —O—SO$_2$—O—, —O—SO—O—, —PH—, —P(CH$_3$)—, —PO$_3$—, —NH—, —N(CH$_3$), and mixtures thereof.

16. The water-soluble or water-swellable copolymer of claim 6, wherein the repeating units A, B, C, and D originate from the group consisting of acrylamide, methacrylamide, ethylene oxide, propylene oxide, AMPS, acrylic acid, methacrylic acid, methyl methacrylate, acrylonitrile, maleic acid, vinyl acetate, styrene, 1,3-butadiene, isoprene, isobutene, diethylacrylamide, diisopropylacrylamide, and mixtures thereof.

17. The water-soluble or water-swellable copolymer of claim 6, wherein the repeating units A, B, C, and D originate from ethylene oxide and/or propylene oxide.

18. The water-soluble or water-swellable copolymer of claim 6, wherein v, w, x, and z independently of one another amount to from 1 to 30.

19. A water-soluble or water-swellable copolymer obtained by free-radical copolymerization of a) 50 to 99% by weight of acryloyldimethyltaurine and/or acrylcyldimethyltaurates based on a total weight of said copolymer, said acryloyldimethyltaurine and/or acryloyldimethyltaurutes having a degree of neutralization of more than 80%, and b) one or more olefinically unsaturated, cationic comonomers containing at least one oxygen, nitrogen, sulfur or phosphorus atom and having a molecular weight of less than 500 g/mol, with or in the presence of at least one component selected from:

c) one or more at least monofunctional, silicon-containing component capable of free-radical polymerization, or e) one or more at least monofunctional, fluorine-containing component capable of free-radical polymerization, crosslinking macromonomer each possessing at least one oxygen, nitrogen, sulfur or phosphorus atom and having a number-average molecular weight of greater than or equal to 200 g/mol, the macromonomers not being a silicon-containing component c) or fluorine-containing component e) said free-radical polymerization taking place in the absence of a polymeric additive.

20. The water-soluble or water-swellable copolymer of claim 19, wherein the comonomer is crosslinking.

21. The water-soluble or water-swellable copolymer of claim 19, wherein the macromonomer is crosslinking.

22. The water-soluble or water-swellable copolymer of claim 19, wherein the polymeric additive is selected from the group consisting of polyalkylene glycol, alkylpolyglycol, and mixtures thereof or a homopolymer or copolymer of a compound selected from the group consisting of N-vinylformamide, N-vinylacetemide, N-vinylpyrrolidone, ethylene oxide propylene oxide, N-vinylpyrrolidone, ethylene oxide propylene oxide, acryloyldimethyltaurine, N-vinylcaprolactam, N-vinylmethylacetamide, acrylamide, acrylic acid, methacrylic acid, N-vinylmorpholide, hydroxymethyl methacrylate, diallyldimethylammonium chloride (DADMAC),

[2-(methacryloyloxy)ethyl]trimethylammonium chloride (MAPTAC), and mixtures thereof.

* * * * *